United States Patent [19]
Abadi

[11] Patent Number: 6,076,661
[45] Date of Patent: Jun. 20, 2000

[54] PACKING SYSTEM FOR CONDOMS

[76] Inventor: Max Marvin Abadi, Carrera 68 No. 21-85, Santa Fé de Bogotá, Colombia

[21] Appl. No.: 08/891,317

[22] Filed: Jul. 9, 1997

[51] Int. Cl.[7] ............................ B65D 85/14; A45C 11/24
[52] U.S. Cl. ................................. 206/69; 206/37; 206/38
[58] Field of Search ................................. 206/69, 37, 38, 206/37.1, 38.1; 128/844

[56] References Cited

U.S. PATENT DOCUMENTS

| | | | |
|---|---|---|---|
| 2,332,857 | 10/1943 | Karg | 206/69 |
| 4,037,716 | 7/1977 | Marks | 206/38 |
| 4,286,641 | 9/1981 | Watson | 206/37 X |
| 4,805,820 | 2/1989 | Kearney et al. | 206/37 X |
| 4,964,416 | 10/1990 | Foldesy | 128/844 C |
| 5,328,026 | 7/1994 | Newman | 206/38 X |
| 5,437,286 | 8/1995 | Stratton | 206/69 X |

FOREIGN PATENT DOCUMENTS 823318  7/1949  Germany ................................ 206/69

*Primary Examiner*—Bryon P. Gehman
*Attorney, Agent, or Firm*—Banner & Witcoff, Ltd.

[57] ABSTRACT

A card, very similar to a credit card, which is appropriate to receive a plural number of rolled condoms, and then covered to give the appearance of a credit card. In the preferred form polyethylene condoms, which are much thinner and allow an optimum height between 2.0 to 2.5 mm. The invention is designed to allow each condom to be in its own separate cavity, thereby making it individually removable. Each cavity is covered by a very thin layer which may be of any appropriate plastic, sealed using any technique known in the art. The card itself may be manufactured of any appropriate material, but preferably an injected plastic such as PVC or polyethylene, which allows the necessary cavities for each condom to be easily formed.

7 Claims, 5 Drawing Sheets

PACKING SYSTEM FOR CONDOMS

TECHNICAL LEVEL

Condoms have been a highly favored alternative among men who wish to take part in sexual activities, in order to fight sexually transmitted diseases and avoid pregnancy in their partner. However, although the condom has proven useful in preventing the mentioned consequences, there is great apprehension among men regarding its use for several reasons, which include: loss of sensitivity for both the man and his partner, inconvenience in putting it on, and the social stigma involved in carrying a condom. It is mainly the latter disadvantage that my invention addresses.

All condoms are currently packed by rolling them and placing them in a plastic wrapper, which helps protect the condom from physical and chemical damage, including that caused by dryness and ultraviolet rays. However, being rolled and inside a plastic wrapper, it is very common that when placed inside a wallet (which is apparently the most discreet place for it), a high relief ring appears on the surface of the wallet, caused by the condom, being rolled and pressed against the walls of said wallet. This often causes great embarrassment and joking when the wallet is seen in a social environment, and may send a totally erroneous message to the partner. The same can occur in the event that it is not carried in the wallet, since practically everybody knows condom packs by sight. It is, therefore, a simple fact that in our society we try to conceal the condom as long as it is not in use, and therefore there is a great need for a very discreet form of packing, but which is at the same time sufficiently resistant to avoid damage to the condom.

On the other hand, the fact that many men carry condoms in their wallet is their main cause for degradation due to temperature and pressure on latex condoms, which are the most common in the market. One solution at the technical level has been to use polyurethane or a polyolefin, as I suggest in my Colombian Patent Application No. 94011.576 which is a counterpart of my U.S. patent application now issued as U.S. Pat. No. 5,579,784.

OBJECT OF THE INVENTION

The main object of this invention is to resolve the problems described above at the technical level. Specifically, the object of this invention is to provide a packing system for condoms which helps the user to prevent third parties from knowing that he is carrying a condom. Likewise, it is another object of this invention to provide a packing system for condoms which enables carrying them securely in a compact place, such as a wallet, without any degradation in same. Finally, another object of this invention is to provide a condom packing system which enables carrying condoms in a very discreet and elegant way.

BRIEF DESCRIPTION OF THE INVENTION

My invention basically comprises a card, very similar to a credit card, which can receive a plural number of rolled condoms, and is then covered to give the appearance of a credit card. Given the thinness of a credit card, it is not advisable to use latex condoms, since when rolled they are too thick for this invention. In the preferred form of the invention, I use polyethylene condoms, which are much thinner and allow me to obtain an optimum height from 2.0 to 2.5 mm.

My invention is designed to allow each condom to be in its own separate cavity, thus being individually removable. Each cavity is covered by a very thin layer made of any appropriate plastic, sealed using any technique known in the art. The card itself may be manufactured from any appropriate material, but preferably an injected plastic such as PVC or polyethylene, which easily allows the formation of the necessary cavities for each condom.

DETAILED DESCRIPTION OF THE INVENTION

To manufacture the card itself, a thin sheet of rigid, but sufficiently plastic, material is used, trying to duplicate, insofar as possible, the characteristics of a credit card. It has been found that injectable plastics, preferably PVC or polyethylene, are optimal for this invention. The cards are cut from this sheet, with dimensions of 8.5 by 5.4 cm, similar to those of a credit card. The thickness of the card is determined by the condom which is to be used, but in the preferred form a range of 1.8 to 5.0 mm, and preferably between 2.0 and 2.5 mm, can be used. The cavities on the card are formed by using a die which, by pressing the plastic, leaves the proper cavity, the dimensions and shape of which can vary depending on the needs of the packing and the condom. The number of cavities can also vary depending on the number of condoms which are to be included in the card.

The card can also be created by injecting it in a mold, which permits cards to be produced with the cavities already incorporated. This is the system used in the preferred form of my invention, since this substantially reduces production costs. Once the card is ready, the condoms can be placed in the cavities, together with any lubricant or other additive one wishes to add (e.g. spermicide). As mentioned above, given the dimensions, it is not commercially realistic to use latex condoms, since they are too thick when rolled (6–8 mm), thereby creating the need for a card almost one centimeter thick, which would have no similarity to a credit card.

Figure 3:
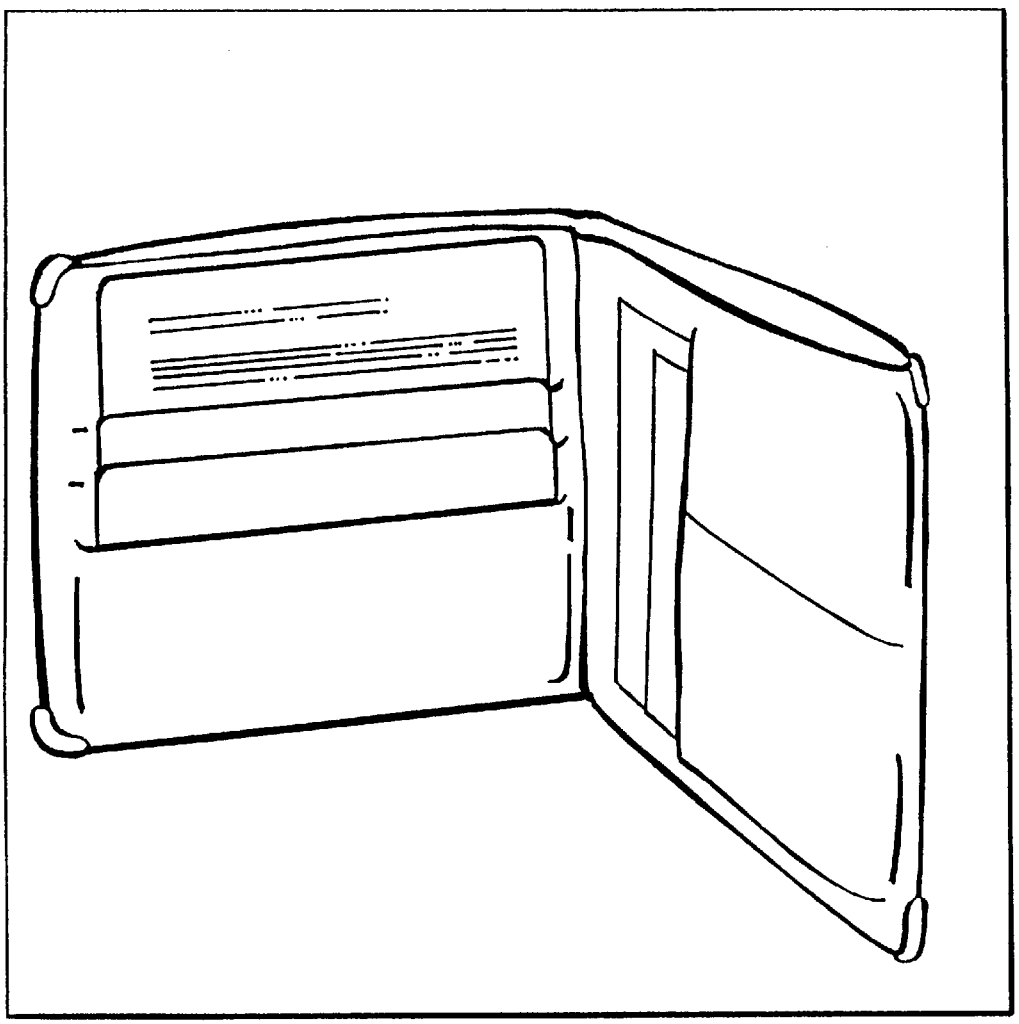
FIG. 3: The same card placed inside a wallet, thus giving the appearance of a credit card.
Figure 4:
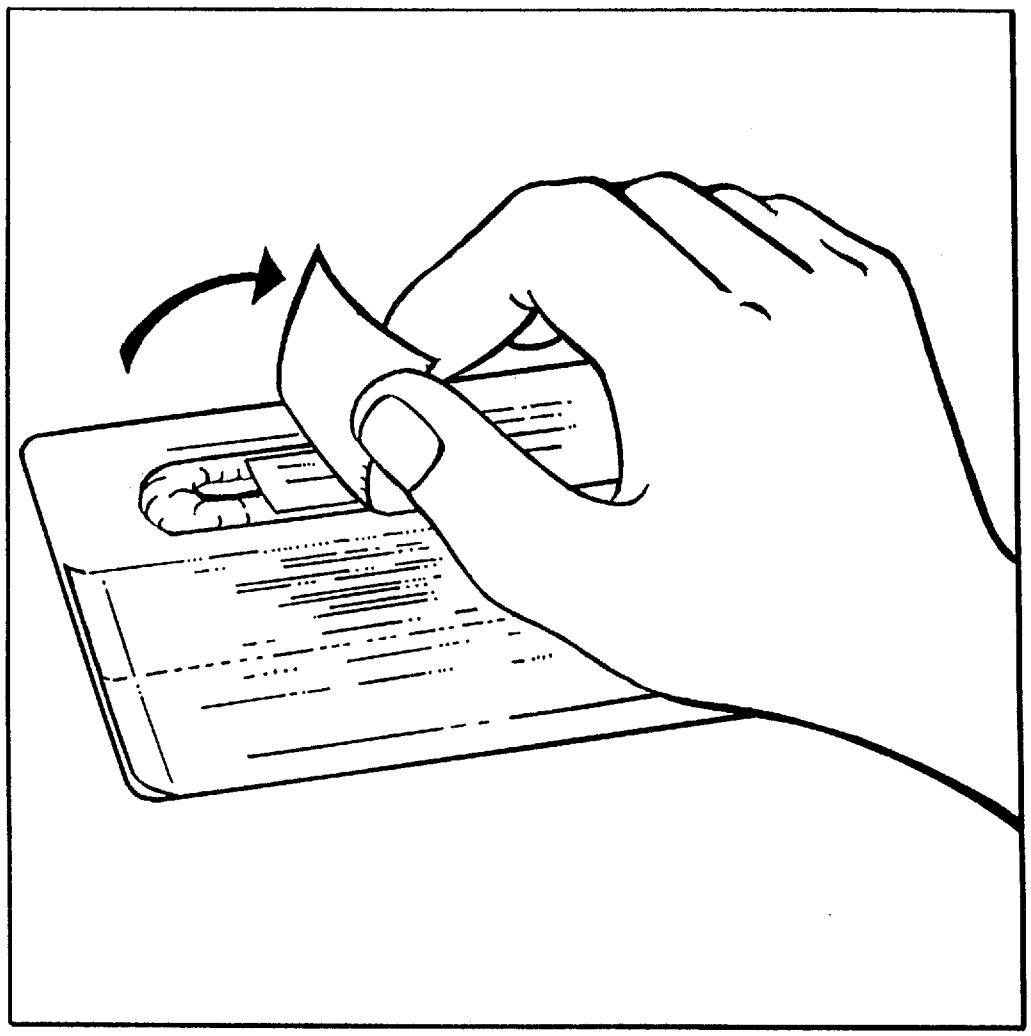
FIG. 4: Shows the user removing one of the adhesive covers over one of the cavities where the condom is kept.

Once the condoms are placed in the cavities, and the other additives considered desirable have been incorporated, the card is finished by covering it with a very thin sheet which is adhered to the card by using any appropriate technique, which may include an external adhesive (glue, adhesive, etc.); or a mechanical closure system which may include the use of heat and pressure, ultrasound or any other similar system. The sheet can preferably be manufactured so as to permit that when separating it from the card, it only uncovers one cavity at a time (see FIG. 4). this can be accomplished by properly pre-perforating the sheet, so that in separating the sheet over a cavity, it tears over the pre-perforated line, as shown in FIG. 4, leaving the other cavities covered. It has been found that polyethylene and PVC are appropriate materials for this sheet. In order to facilitate the opening of a cavity, it is useful to leave a small corner of the sheet without adhesive for each cavity thereby allowing the user to start from the corner. The sheet may be transparent, but preferably should be printed in order to give the card the external appearance of a credit card (see FIG. 1 and FIG. 3). Finally, although it is not necessary, another similar sheet can also be used to cover the back of the card, in order to give the card a consistent finish.

Figure 1:
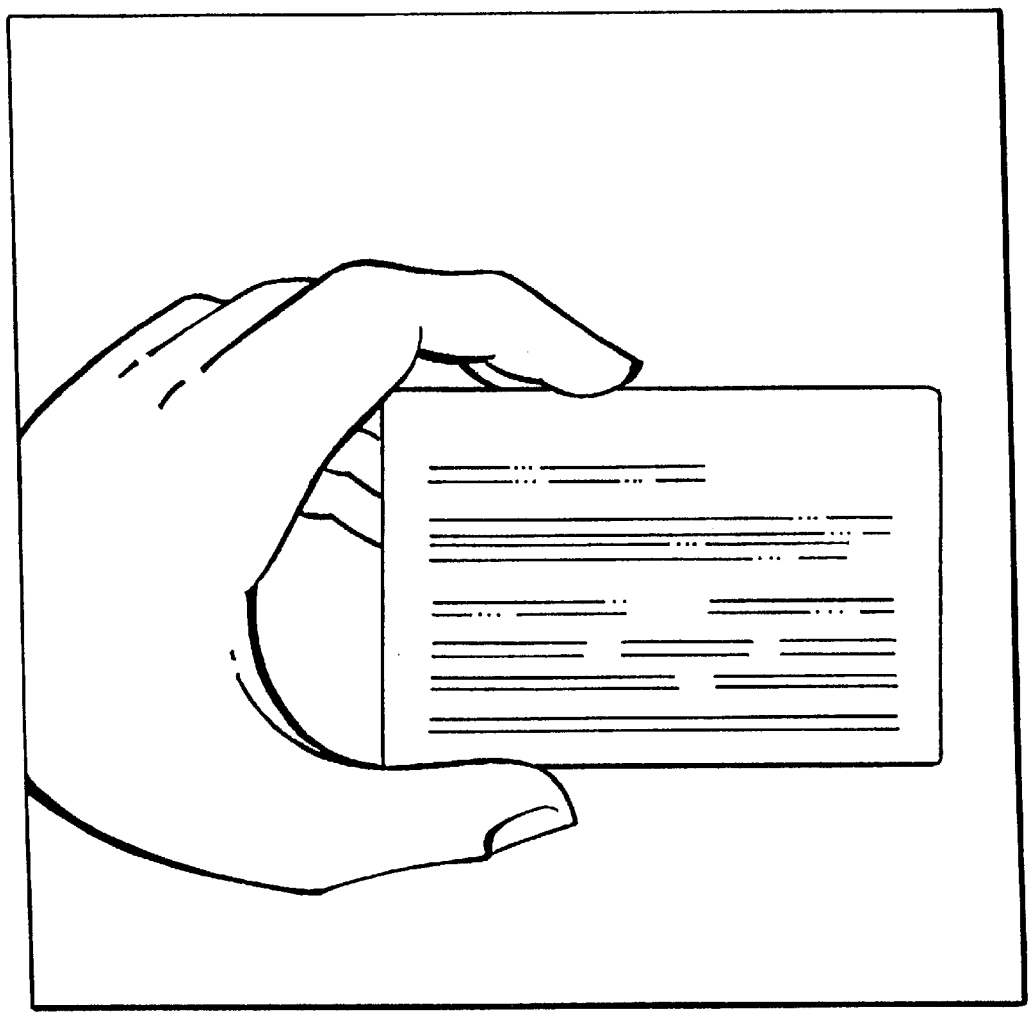
FIG. 1: Front view of the card with a cover giving the appearance of a credit card.
Figure 2:
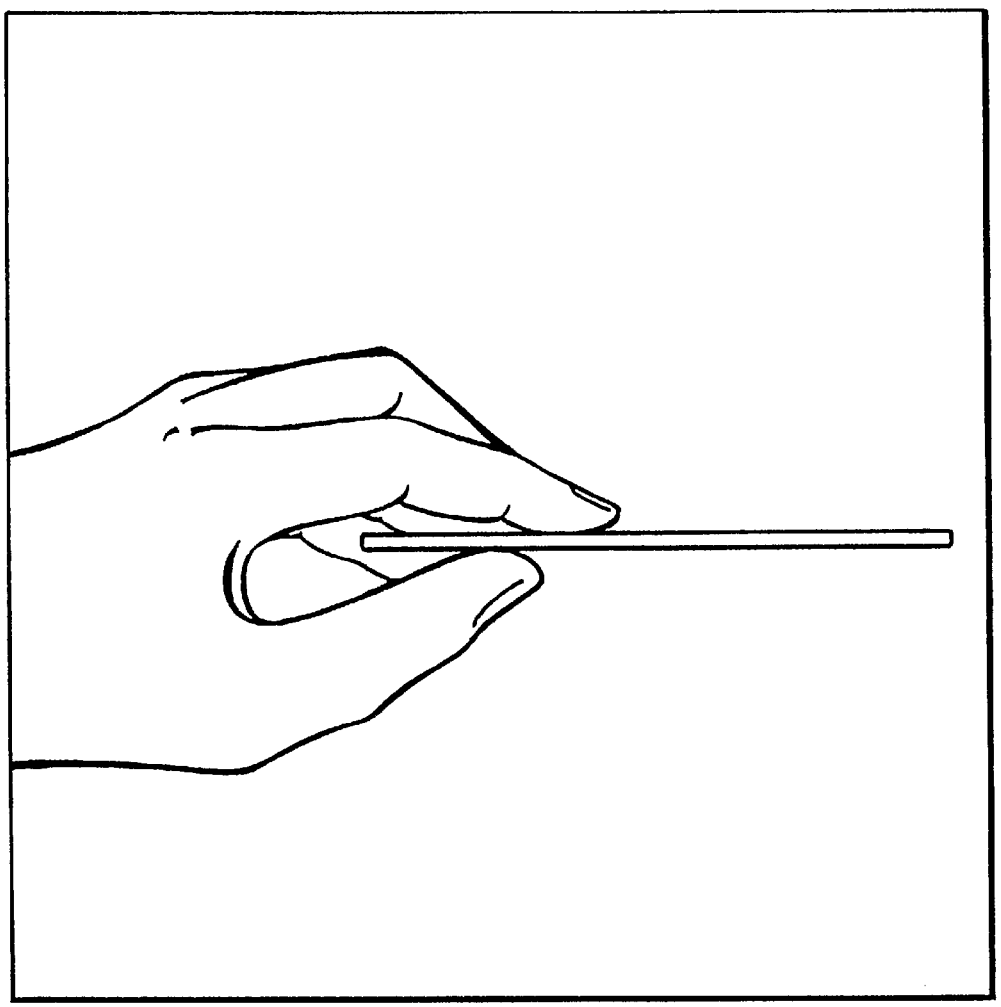
FIG. 2: Side view of the same card, showing the thinness of the package.
Figure 5:
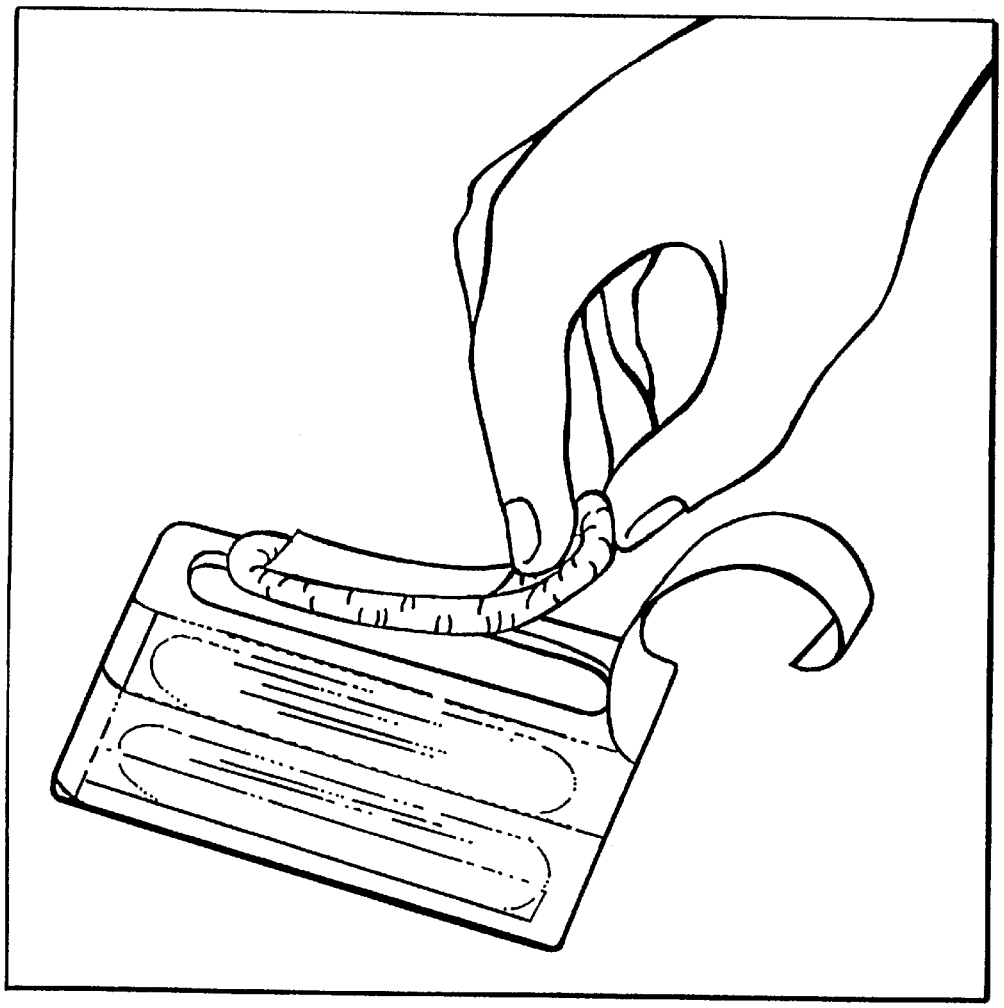
FIG. 5: Shows the user removing the condom, individually, from its cavity for eventual use.

To use the condoms, it is simply necessary to follow the two steps shown in FIGS. 4 and 5, that is, to remove the sheet covering the cavity and withdraw the condom. As shown in FIGS. 1, 2 and 3, the card is indistinguishable from an ordinary credit card, which makes it highly discreet. It also allows the condoms to be safely carried in a wallet, avoiding their physical or chemical damage. And moreover, if polyethylene condoms are used, a very long life is secured for the condoms in this packing.

Those with technical expertise will appreciate that there are many evident variations and modifications of the invention described above in the descriptive chapter and in the drawings, and this is only a preferred form. It will be understood that the scope and limitation of the invention is defined only through the following claims:

What is claimed is:

1. A multi-condom package, comprising:
    a generally flat rectangular card body defining a plurality of elongated cavities extending generally parallel to each other between opposite edges of said card body;
    a condom snugly fitted into each of said elongated cavities, in a rolled and folded condition; and
    a sheet adhered to a first side of said card body, said sheet including a plurality of disposable tear-away strips overlying and removably sealing respective ones of said elongated cavities to thereby form a plurality of sealed independently openable condom containing storage compartments.

2. A multi-condom package according to claim 1, wherein said sheet comprises perforation lines defining said disposable tear-away strips.

3. A multi-condom package according to claim 2, wherein said disposable tear-away strips have end portions which are not adhered to said card body, which may be grasped by hand to initiate removal of the tear-away strips.

4. A multi-condom package according to claim 1, said package comprising three said elongated cavities and condoms contained therein, and said sheet comprising three said disposable tear-away strips overlying and removably sealing respective ones of said three elongated cavities, to thereby form three said sealed independently openable condom containing storage compartments.

5. A multi-condom package according to claim 1, wherein each said condom is made of polyethylene and the thickness of the package is in the range of approximately 2.0–2.5 mm.

6. A multi-condom package according to claim 1, further comprising, within each cavity, at least one of a lubricant and a spermicide.

7. A multi-condom package according to claim 1, further comprising a second sheet adhered to a side of said card body opposite said first side.

* * * * *